United States Patent
Herrmann et al.

(10) Patent No.: US 10,646,416 B2
(45) Date of Patent: May 12, 2020

(54) MICROCAPSULES CONTAINING A GAS-RELEASING PHOTOLABILE COMPOUND AND USES THEREOF

(71) Applicant: FIRMENICH SA, Satigny (CH)

(72) Inventors: Andreas Herrmann, Geneva (CH); Damien Berthier, Geneva (CH); Nicolas Paret, Geneva (CH); Alain Trachsel, Geneva (CH)

(73) Assignee: Firmenich SA, Satingy (CH)

( * ) Notice: Subject to any disclaimer, the term of this patent is extended or adjusted under 35 U.S.C. 154(b) by 275 days.

(21) Appl. No.: 14/893,526

(22) PCT Filed: May 21, 2014

(86) PCT No.: PCT/EP2014/060476
§ 371 (c)(1),
(2) Date: Nov. 23, 2015

(87) PCT Pub. No.: WO2014/187874
PCT Pub. Date: Nov. 27, 2014

(65) Prior Publication Data
US 2016/0120773 A1 May 5, 2016

(30) Foreign Application Priority Data
May 22, 2013 (EP) .................................... 13168768

(51) Int. Cl.
| | | |
|---|---|---|
| *A61K 8/11* | (2006.01) | |
| *C11D 3/50* | (2006.01) | |
| *A61K 8/35* | (2006.01) | |
| *A61K 8/365* | (2006.01) | |
| *A61K 8/40* | (2006.01) | |
| *A61Q 13/00* | (2006.01) | |
| *B01J 13/16* | (2006.01) | |
| *B01J 13/06* | (2006.01) | |
| *C08G 18/76* | (2006.01) | |
| *A61K 8/87* | (2006.01) | |
| *C11B 9/00* | (2006.01) | |
| *D21H 21/14* | (2006.01) | |
| *A61Q 5/02* | (2006.01) | |
| *A61Q 5/06* | (2006.01) | |
| *A61Q 15/00* | (2006.01) | |
| *A61Q 19/08* | (2006.01) | |

(52) U.S. Cl.
CPC .................. *A61K 8/11* (2013.01); *A61K 8/35* (2013.01); *A61K 8/365* (2013.01); *A61K 8/40* (2013.01); *A61K 8/87* (2013.01); *A61Q 13/00* (2013.01); *B01J 13/06* (2013.01); *B01J 13/16* (2013.01); *C08G 18/7642* (2013.01); *C11B 9/00* (2013.01); *C11D 3/505* (2013.01); *D21H 21/14* (2013.01); *A61K 2800/10* (2013.01); *A61K 2800/22* (2013.01); *A61K 2800/56* (2013.01); *A61Q 5/02* (2013.01); *A61Q 5/06* (2013.01); *A61Q 15/00* (2013.01); *A61Q 19/08* (2013.01)

(58) Field of Classification Search
CPC ........ A61K 8/11; A61K 2800/10; A61K 8/87; A61K 8/40; A61K 8/365; A61K 8/35; A61K 2800/56; A61K 2800/22; D21H 21/14; C11B 9/00; C11D 3/505; A61Q 13/00; A61Q 19/08; A61Q 15/00; A61Q 5/06; A61Q 5/02; C08G 18/7642; B01J 13/16; B01J 13/06
See application file for complete search history.

(56) References Cited

U.S. PATENT DOCUMENTS

| 3,301,439 A | 1/1967 | Kosar et al. |
|---|---|---|
| 4,396,670 A | 8/1983 | Sinclair et al. |
| 2003/0129212 A1* | 7/2003 | Herrmann ................ A61K 8/37 424/405 |
| 2007/0202063 A1 | 8/2007 | Dihora et al. |
| 2008/0176780 A1* | 7/2008 | Warr .................... A61K 8/0237 510/103 |

FOREIGN PATENT DOCUMENTS

| EP | 1 741 775 B1 | 4/2009 |
|---|---|---|
| GB | 2 432 843 A | 6/2007 |
| GB | 2 432 850 A | 6/2007 |
| GB | 2 432 851 A | 6/2007 |
| GB | 2 432 852 A | 6/2007 |
| WO | WO 99/60990 A2 | 12/1999 |
| WO | WO 01/041915 A1 | 6/2001 |
| WO | WO 2005/054422 A1 | 6/2005 |
| WO | WO 2007/062733 A1 | 6/2007 |
| WO | WO 2007/062833 A1 | 6/2007 |
| WO | WO 2008/016684 A1 | 2/2008 |
| WO | WO 2011/154893 A1 | 12/2011 |
| WO | WO 2011/161618 A1 | 12/2011 |
| WO | WO 2012/104262 A1 | 8/2012 |
| WO | WO 2013/079435 A1 | 6/2013 |

OTHER PUBLICATIONS

Hermnann, Photochem. Photobiol. Sci., 2012, 11, p. 446.*
Baum Reactivity of Excited States, Butyrophenones, JACS 1996, p. 2652.*
Mathiowitz , J. of Applied Polymer Sci. 1981, p. 809.*
International Search Report and Written Opinion, application PCT/EP2014/060476, dated Jul. 25, 2014.
Banerjee et al., Tetrahedron, 1999, vol. 55, pp. 12699-12710.
Blake et al., Organic Letters, 2006, vol. 8, pp. 1057-1060.
Bonatz et al., Acta Polymerica, 1989, vol. 40, pp. 683-690.
Bône et al., Chimia, 2011, vol. 65, No. 3, pp. 177-181.
Braslaysky, IUPAC-Pure and Applied Chemistry, 2007, vol. 79, pp. 293-465.

(Continued)

*Primary Examiner* — Matthew P Coughlin
*Assistant Examiner* — Thurman Wheeler
(74) *Attorney, Agent, or Firm* — Armstrong Teasdale LLP

(57) ABSTRACT

The present invention relates to water-dispersible microcapsules that include an oil phase, e.g. a perfume, containing a photolabile compound capable of generating a gas upon exposure to light. The gas is able to cause an extension or the breaking of the microcapsule allowing the release of the oil phase and thus increasing the long-lastingness of the odor perception. The present invention concerns also the use of such microcapsules in perfumery as well as the perfuming compositions or perfumed articles that include such microcapsules therein to provide a prolonged release of fragrant molecules.

21 Claims, 1 Drawing Sheet

(56) References Cited

OTHER PUBLICATIONS

Dietrich et al., Acta Polymerica, 1989, vol. 40, pp. 243-251.
Dietrich et al., Acta Polymerica 1989, vol. 40, pp. 325-331.
Dietrich et al. Acta Polymerica 1990, vol. 41, pp. 91-95.
Gilman et al., J. of the American Chemical Society, 1957, vol. 79, pp. 2150-2153.
Herrmann, Angewandte Chemie, Aug. 3, 2007, vol. 46, pp. 5836-5863.
Klan et al., Chemical Reviews, 2013, vol. 113, pp. 119-191.
Lee et al., J. of Microencapsulation, 2002, vol. 19, pp. 559-569.
Literak et al., Photochemical and Photobiological Sciences, 2005, vol. 4, pp. 43-46.
Manolov, Pharmazie, 2006, vol. 61, pp. 511-516.
Petit et al., Organic Letters, 2012, vol. 14, No. 24, pp. 6366-6369.
Schlegel et al., J. of Medicinal Chemistry, 1984, vol. 27, pp. 1682-1690.
Sieh et al., J. of the American Chemical Society, 1980, vol. 102, pp. 3883-3887.
Takemiya et al., J. of the American Chemical Society, 2006, vol. 128, pp. 14800-14801.

* cited by examiner

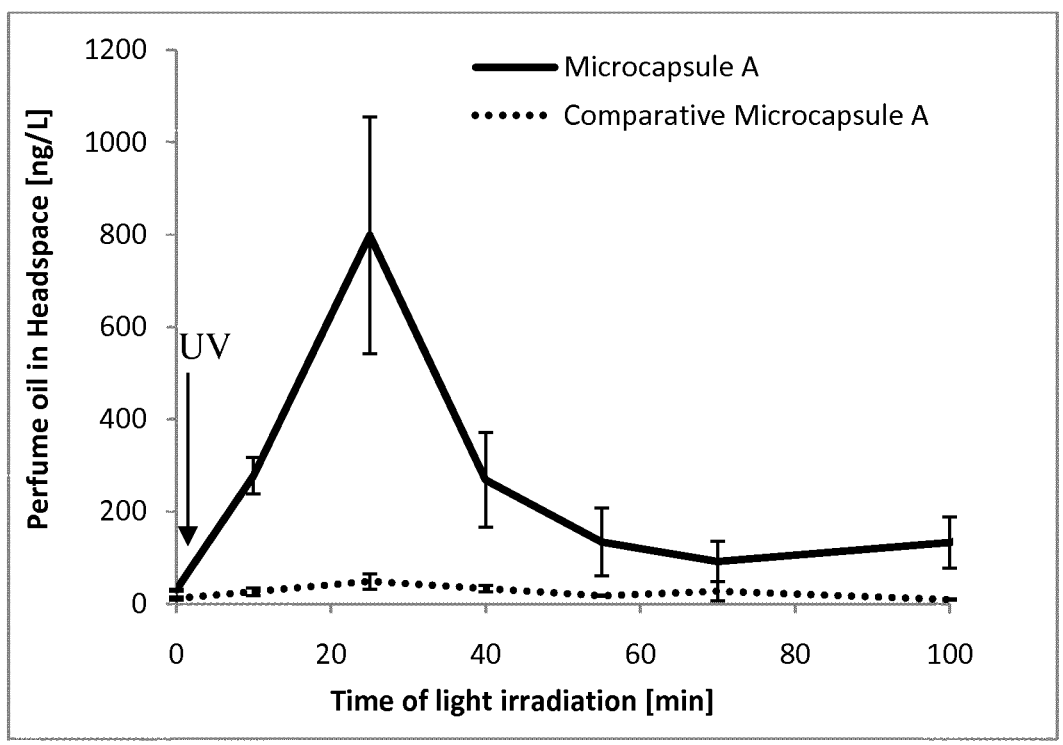

MICROCAPSULES CONTAINING A GAS-RELEASING PHOTOLABILE COMPOUND AND USES THEREOF

This application is a 371 filing of International Patent Application PCT/EP2014/060476 filed May 21, 2014, which claims the benefit of European patent application no. 13168768.3 filed May 22, 2013.

TECHNICAL FIELD

The present invention relates to water-dispersible microcapsules capable of increasing the long-lastingness of active compounds and of releasing those compounds upon exposure to light. The invention concerns the encapsulation of photolabile compounds capable of releasing a gas, so as to trigger the release of an oil phase containing at least one active compound capable of bringing a benefit or effect into its surrounding environment, and the use of the resulting microcapsules in consumer products.

PRIOR ART

One of the problems faced by the perfume industry lies in the relatively rapid loss of the olfactive benefit provided by odoriferous compounds as a result of their volatility, particularly that of "top-notes". Also, some fragrance ingredients can be unstable in applications of functional perfumery and get lost due to degradation or to rapid evaporation. These problems are often tackled through the use of delivery systems, e.g. capsules containing a perfume, to release the fragrance in a controlled manner.

Encapsulation of the fragrance can at least partially solve the evaporation problem, but many types of microcapsules are known to lose parts of the fragrance during storage, via diffusion through their shells or walls or as a result of the nature of the consumer product into which they are incorporated and which contains surface active ingredients capable of causing leakage of the perfume.

However, to perceive the perfume with such systems one either needs to mechanically break the microcapsules or to generate a spontaneous leakage of the perfume out of the capsules at the desired time. In the first case, the olfactive experience is limited to scratching episodes, while in the second case, one usually encounters problems of performance due to issues related to the limited shelf-life of the consumer product containing the microcapsules.

It is therefore desirable to create new systems capable of solving or at least reducing the above-cited problems and the present invention provides such a solution.

According to the invention, the fragrance is encapsulated within a solid shell or membrane or yet is part of a matrix system together with a compound which is able to cause an extension or the breaking of the microcapsule and thus triggering the olfactive experience without requiring a scratching episode or relying on a leakage phenomenon which is difficult to control.

The same problem applies to many other benefit agents.

We have now been able to establish that the encapsulation of a photolabile compound able to generate a gas inside microcapsules resulted in the desired effect, i.e. the spontaneous extension or breaking of the microcapsule upon exposure to light. This effect is surprising because one might have expected that the unfavorable transparency of the capsule shell or wall to light would have reduced the efficiency of the photoreaction necessary to release the gas.

DESCRIPTION OF THE INVENTION

One object of the present invention is a non-diffusive microcapsule comprising:
a) a core comprising, or even consisting of:
   an oil phase;
   at least one photolabile compound capable of generating, upon exposure to light at a wavelength comprised between 900 and 300 nm, a gas selected among the group consisting of CO, $CO_2$, $N_2$ and $C_2$-$C_4$ alkenes; and
   optionally comprising at least one photo-catalyst; and
b) a shell surrounding said core and formed by interfacial polymerization or by a phase separation process induced by polymerization or by coacervation.

For the sake of clarity, by the expression "microcapsule", or the similar, in the present invention it is meant that the microcapsule comprises an external solid oligomer-based shell or wall and an internal continuous oil phase enclosed by the external shell. In other words, encapsulates such as core-shell systems (e.g coacervates) or systems with a matrix morphology (e.g. extrudates or porous solid phases containing droplets of a liquid) are considered to be part of the invention. By the expression "core-shell", it is meant that the oil phase is surrounded by a shell whereas by the expression "matrix morphology" it is meant that the oil phase is dispersed in a matrix.

Preferably the microcapsule is a core-shell system.

For the sake of clarity, by the expression "non-diffusive" or the similar in the present invention it is meant that the shell or wall of the microcapsule is not permeable to the oil phase inside the microcapsule. By the expression "not permeable", it is meant that the release of the oil phase in absence of light shell is negligible or not perceivable (i.e. below the odor threshold).

By the term "oil phase" we mean here a liquid or a solution, at 20° C. and 1 atm of pressure, and which is capable of bringing a benefit or effect into its surrounding environment, and in particular comprises a perfuming, flavoring, cosmetic, skin caring, malodor counteracting, bactericide, fungicide, pharmaceutical or agrochemical ingredient, a diagnostic agent and/or an insect repellent or attractant.

Said oil phase can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient, a diagnostic agent and/or as an insect repellent or attractant.

Preferably, said oil phase can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient and/or as an insect repellent or attractant.

Practically, the invention is carried out exactly in the same manner, independently of the exact properties of the oil phase. Therefore, it is understood that, even if the invention will be further illustrated herein below with a specific reference to "perfuming" ingredients, the below embodiments are also applicable to other oils (i.e. it is possible to replace the expression "perfuming" with "flavoring", "cosmetic", "skin caring", "malodor counteracting", "bactericide", "fungicide", "pharmaceutical", "agrochemical", "diagnostic agent", "insect attractant" or with "insect repellent" for instance).

According to a particular embodiment of the invention, the invention's core-shell microcapsule is particularly useful when the oil phase comprises a perfuming oil, i.e. a single perfume ingredient or a perfuming composition. A "perfuming ingredient" is a compound, which is of current use in the perfumery industry, i.e. a compound which is used as active ingredient in perfuming preparations or compositions in order to impart a hedonic effect. In other words, such a perfuming ingredient must be recognized by a person skilled in the art of perfumery as being able to impart or modify in a positive or pleasant way the odor of a composition, and not just as having an odor. For the sake of clarity, the definition of a perfuming ingredient is meant to include also compounds that do not necessarily have an odor but are capable of modulating the odor. For the sake of clarity, the definition of perfuming ingredient is meant to include also pro-perfumes, i.e compounds which upon decomposition liberate a perfuming ingredient. A "perfuming composition" is a mixture of compounds including at least two perfuming ingredients.

In general terms, these perfuming ingredients belong to chemical classes as varied as alcohols, lactones, aldehydes, ketones, esters, ethers, ester nitriles, terpenoids, nitrogenous or sulphurous heterocyclic compounds and essential oils, and said perfuming ingredients can be of natural or synthetic origin. Specific examples of such perfuming ingredients can be found in reference texts such as the book by S. Arctander, "Perfume and Flavor Chemicals", published by the author, Montclair (New Jersey, USA), 1969, or its more recent versions, or in other work of a similar nature, as well as in the abundant patent literature in the field of perfumery. They are well known to the person skilled in the art of perfuming consumer products, that is, of imparting a pleasant odor to a consumer product.

In particular such perfuming oil may comprise also solvents and adjuvants of current use in perfumery.

By "solvents of current use in perfumery" we mean here a material which is practically neutral from a perfumery point of view, i.e. that does not significantly alter the organoleptic properties of perfuming ingredients and is generally not miscible with water, i.e. possesses a solubility in water below 10%, or even below 5%. Solvents commonly used in perfumery, such as for example dipropyleneglycol, diethyl phthalate, isopropyl myristate, benzyl benzoate, 2-(2-ethoxyethoxy)-1-ethanol or ethyl citrate, limonene or other terpenes, isoparaffins such as those known under the trademark Isopar® (origin: Exxon Chemical) or glycol ethers and glycol ether esters such as those known under the trademark Dowanol® (origin: Dow Chemical Company), are suitable solvents for the purposes of the invention.

By "adjuvants of current use in perfumery" we mean here an ingredient capable of imparting additional added benefits such as a color, chemical stability, etc. A detailed description of the nature and type of adjuvant commonly used in perfuming bases cannot be exhaustive, but it has to be mentioned that said ingredients are well known to a person skilled in the art.

Said oil phase can be included at various amounts depending on its nature and the strength of the aimed olfactive effect. Typically, the microcapsules comprise, based on the total microcapsule weight, from about 1% to about 99% by weight, of oil phase. Preferably the microcapsules comprise from about 20% to about 96% of oil phase.

The component a) of the microcapsules according to the invention also comprises at least one photolabile compound capable of generating, upon exposure to the light, a gas selected among the group consisting of CO, $CO_2$, $N_2$ and $C_2$-$C_4$ alkenes (also referred as "photolabile compound"). According to any embodiment of the invention, said photolabile compound can be advantageously selected among the group consisting of photolabile compounds comprising an alkyl aromatic ketone, a di-aromatic ketone, a N—N=N (triazene) moiety or a carbonate derivative. For the sake of clarity α-ketoacids, α-ketoesters and azido compounds are not included in the preset application.

Said compounds are well known to a person skilled in the art and can be found in the literature, as for example in P. Klán et al., Chemical Reviews, 2013, vol. 113, pages 119-191.

According to a particular embodiment of the invention, said photolabile compound upon decomposition generates residues which are odorless.

For the sake of clarity, by the expression "odorless compound", or the similar, in the present invention it is meant that said residues have a vapor pressure below 2.0 Pa, as obtained by calculation using the program EPI suite (4.0); EPA (US Environmental Protection Agency) and Syracuse Research Corporation (SRC), 2000. Preferably said vapor pressure is below 1.0 Pa, below 0.1 Pa, or even below 0.01 Pa, in other words, said corresponding residues are not a perfuming one.

In particular one can mention as photo-labile compound comprising a CO moiety an alkyl aromatic ketone, which liberates upon photolysis a $C_2$-$C_4$ alkene, and being of formula

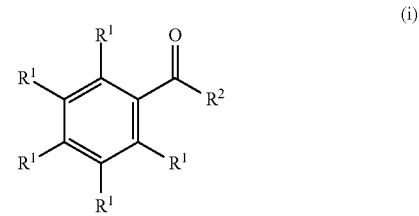

(i)

wherein each $R^1$ represents, independently of each other, a hydrogen atom, a fluorine or chlorine atom, a hydroxyl, or amino group, or a $C_{1-2}$ alkyl, $C_{1-2}$ alkoxy, $C_{1-2}$ dialkylamino or $COR^{2'}$ group wherein $R^{2'}$ represents a hydrogen atom or a $C_{1-4}$ alkyl group, provided that at least two $R^1$ represent a hydrogen atom; or two adjacent $R^1$, when taken together, represent a $OCH_2O$ group, a $OCH_2CH_2O$ group or a $C_{3-4}$ alkanediyl group, optionally substituted with one to four methyl groups; and wherein $R^2$ represents a propyl, n-butyl or sec-butyl group.

According to any embodiment of the invention, said photolabile compounds of formula (i) are those wherein $R^1$ represents a hydrogen atom, or a $C_{1-2}$ alkyl, $C_{1-2}$ alkoxy or $COR^{2'}$ group wherein $R^{2'}$ represents a hydrogen atom or a $C_{1-4}$ alkyl group, provided that at least three $R^1$ represent a hydrogen atom; or two adjacent $R^1$, when taken together, represent a $OCH_2O$ group; and
$R^2$ represents a propyl, n-butyl or sec-butyl group.

According to any embodiment of the invention, preferred compounds of formula (i) are butyrophenone, 4-methoxybutyrophenone, 4-hydroxybutyrophenone, 3,4-(methylenedioxy)butyrophenone, valerophenone, 2- and 4-hydroxy-valerophenone and isovalerophenone. Even more preferred is butyrophenone.

In particular one can mention as photo-labile compound comprising a CO moiety a (3-benzoylphenyl)- or (9-oxo-9H-xanthen-2-yl)-acetic acid derivative, which liberates upon photolysis $CO_2$, and being of formula

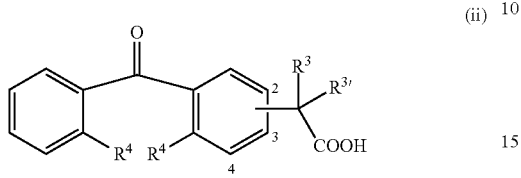

(ii)

with the —$CR^3R^{3'}COOH$ group being either in the 2-, 3- or 4-position and wherein
$R^3$ represents a hydrogen atom, a methyl or a phenyl group;
$R^{3'}$ represents a hydrogen atom or a methyl, a $CH_2OCOCH_3$ or a $CH_2OCOXR'$ group, $R'$ representing a $C_{1-12}$ hydrocarbon group, X represents an O or a S atom or a NR group, R representing a hydrogen atom or a $C_{1-4}$ alkyl group; and
each $R^4$, taken separately, represents a hydrogen atom, or both $R^4$ taken together represent an oxygen atom bridge.

According to any embodiment of the invention, said photolabile compounds of formula (ii) are those wherein the —$CR^3R^{3'}COOH$ group is either in the 2-, 3- or 4-position, preferably in the 2-position;
$R^3$ represents a hydrogen atom or a methyl group;
$R^{3'}$ represents a hydrogen atom or a methyl, a $CH_2OCOCH_3$ or a $CH_2OCOXR'$ group, X represents an O atom or a NR group; and
each $R^4$, taken separately, represents a hydrogen atom, or both $R^4$ taken together represent an oxygen atom bridge.

According to any embodiment of the invention, preferred compounds of formula (ii) are 2-(3-benzoylphenyl)acetic acid, 2-(3-benzoylphenyl)propanoic acid, 2-, 3- or 4-(9-oxo-9H-xanthen-2-yl)acetic acid, 2-, 3- or 4-(9-oxo-9H-xanthen-2-yl)propanoic acid and 3-acetoxy-2-methyl-2-(9-oxo-9H-xanthen-2-yl)propanoic acid.

In particular one can mention as photo-labile compound comprising a CO moiety a carbonate derivative, which liberates upon photolysis $CO_2$, and being of formula

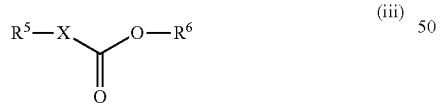

(iii)

wherein X represents an O or a S atom or a NR group, R representing a hydrogen atom or a $C_{1-4}$ alkyl group;
$R^5$ represents
  a $C_{1-16}$ hydrocarbon group optionally comprising one or two oxygen or nitrogen atoms; or
  a group of formula $R^{5'}(X(CO)OR^6)_n$ wherein X and $R^6$ have the same meaning as below, $R^{5'}$ is a $C_{2-12}$ hydrocarbon group and optionally comprising one or two oxygen or nitrogen atoms not directly connected to X and n is an integer comprised between 1 and 4; and
$R^6$ represents a group of formula $C(R^3)_2A$, $R^3$ having the meaning as defined in formula (ii), and A being a group of the formulae

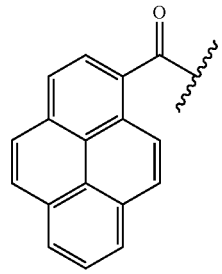

(a)

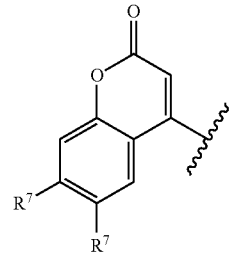

(b)

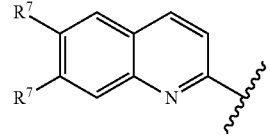

(c)

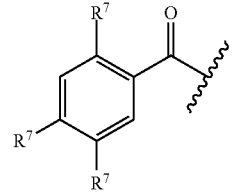

(d)

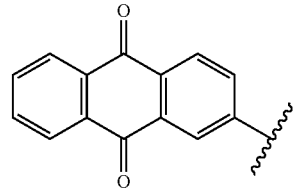

(e)

each $R^7$ represents, independently from each other, a hydrogen or bromine atom, or a $CH_3$, OH, $OCH_3$, $NH_2$, $N(CH_3)_2$, $N(CH_2CH_3)_2$ or $N(CH_2COOH)_2$ group.

According to any embodiment of the invention, said photolabile compounds of formula (iii) are those wherein
X represents an O atom or a NR group;
$R^5$ represents a $C_{1-12}$ hydrocarbon group optionally comprising one or two oxygen or nitrogen atoms; or a group of formula $R^{5'}(X(CO)OR^6)_n$ wherein X and $R^6$ have the same meaning as above, $R^{5'}$ is a $C_{2-12}$ hydrocarbon group, and
$R^6$ represents a 2-oxo-2-(pyren-1-yl)ethyl, (6-bromo-7-hydroxy-2-oxo-2H-chromen-4-yl)methyl, (7-amino-2-oxo-2H-chromen-4-yl)methyl, (7-(dimethylamino)-2-oxo-2H-chromen-4-yl)methyl, (7-(diethylamino)-2-oxo-2H-chromen-4-yl)methyl, (7-hydroxy-2-oxo-2H-chromen-4-yl)methyl, (7-methoxy-2-oxo-2H-chromen-4-yl)methyl, (6,7-dimethoxy-2-oxo-2H-chromen-4-yl)methyl, (6- or 7-(dimethylamino)quinolin-2-yl)methyl, (6- or 7-(diethylamino)quinolin-2-yl)methyl, (6- or 7-hydroxyquinolin-2-yl)methyl, 2-oxo-2-phenylethyl, 2-(4-hydroxyphenyl)-2-oxoethyl, 2-(2-hydroxyphenyl)-2-oxoethyl, 2-(2,5-dimethylphenyl)-2-oxoethyl, 2-oxo-1,2-diphenylethyl or (9,10-dioxo-9,10-dihydroanthracen-2-yl)methyl group.

According to any embodiment of the invention, preferred compounds of formula (iii) are those wherein X represents an O atom;
$R^5$ represents a $C_{1-10}$ hydrocarbon group or a group of formula $R^{5'}(O(CO)OR^6)_n$ wherein
$R^6$ has the same meaning as above, $R^{5'}$ is a $C_{2-8}$ hydrocarbon group, and
$R^6$ represents a 2-oxo-2-(pyren-1-yl)ethyl, (6-bromo-7-hydroxy-2-oxo-2H-chromen-4-yl)methyl, (7-amino-2-oxo-2H-chromen-4-yl)methyl, (7-(dimethylamino)-2-oxo-2H-chromen-4-yl)methyl, (7-(diethylamino)-2-oxo-2H-chromen-4-yl)methyl, (6- or 7-(dimethylamino)quinolin-2-yl)methyl, (6- or 7-(diethylamino)quinolin-2-yl)methyl, 2-oxo-2-phenylethyl, 2-(2-hydroxyphenyl)-2-oxoethyl, 2-(2,5-dimethylphenyl)-2-oxoethyl, or (9,10-dioxo-9,10-dihydroanthracen-2-yl)methyl group.

According to any embodiment of the invention, preferred compounds of formula (iii) are ethyl(2-oxo-2-(pyren-1-yl)ethyl)carbonate, (6-(dimethylamino)quinolin-2-yl)methyl ethyl carbonate, ethyl(2-oxo-2-phenylethyl)carbonate or (9,10-dioxo-9,10-dihydroanthracen-2-yl)methyl ethyl carbonate.

In particular one can mention as photo-labile compound comprising a N—N=N moiety a triazene derivative, which liberates upon photolysis $N_2$, and being of formula

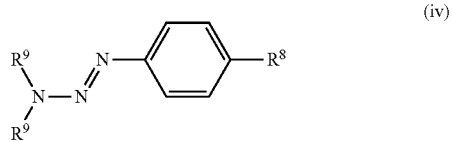

(iv)

wherein each $R^9$, independently of each other, represents a hydrogen atom or a $C_{1-10}$ hydrocarbon group possibly containing an oxygen or nitrogen atom not being adjacent to the nitrogen atom to which said $R^9$ is bound to; or two $R^9$, when taken together, represent a $C_{4-6}$ alkanediyl group, optionally containing one ether group with the O atom not being adjacent to the nitrogen atom of the cycle; and
$R^8$ represents a $R^7$ group, as defined in formula (iii), a carboxylic acid group, a methyl or ethyl carboxylate group, a chlorine atom or a group of formula —Y—$C_6H_4$—N=N—$NR^9_2$ wherein Y represents an O or S atom or a NR group, as defined in formula (ii), or a CO, $CH_2$, HC=CH or $SO_2$ group.

For the sake of clarity, azido compounds are not covered by formula (iv)

According to any embodiment of the invention, said photolabile compounds of formula (iv) are those wherein each $R^9$, independently of each other, represents a $C_{1-6}$ hydrocarbon group possibly containing an oxygen or nitrogen atom not being adjacent to the nitrogen atom to which $R^9$ is bound to; or two $R^9$, when taken together, represent a $C_{4-5}$ alkanediyl group, optionally containing one ether group with the oxygen atom not being adjacent to the nitrogen atom of the cycle; and
$R^8$ represents a hydrogen atom, a methyl group, a methoxy group or a group of formula —Y—$C_6H_4$—N=N—$NR^7_2$ wherein Y represents an O atom or a NR group, as defined in formula (i), or a CO, $CH_2$, HC=CH or $SO_2$ group.

According to any embodiment of the invention, preferred compounds of formula (iv) are 1,3-diphenyltriaz-1-ene, 3-methyl-1-(p-tolyl)triaz-1-ene, 3,3-dimethyl-1-(p-tolyl)triaz-1-ene or 3,3-dimethyl-1-phenyltriaz-1-ene.

It is understood that by " . . . hydrocarbon group . . . " it is meant that said group is consisting of hydrogen and carbon atoms and can be in the form of a linear, branched or cyclic, aromatic, alkyl, alkenyl, or alkynyl group, e.g., a linear alkyl group, or can also be in the form of a mixture of said type of groups, e.g. a specific group may comprise a linear alkyl, a branched alkenyl (e.g. having one or more carbon-carbon double bonds), a (poly)cyclic alkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is meant also a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

For the sake of clarity, by the expression "optionally comprising one or two oxygen or nitrogen atoms", or the similar, in the present invention it is meant that the group to which it is make reference may include in its structure, functional groups such as for examples amines, ethers, acetals, esters, aldehydes, ketones, amides, carboxylates or alcohols.

According to any embodiment of the invention, photolabile compounds that generate a gas selected amongst the group consisting of CO, $CO_2$ and $C_2$-$C_4$ alkenes, are particularly suitable. In particular the compounds of formulae (i) and (iii) are particularly suitable. And more particularly, the compounds of formula (i) are particularly suitable.

According to any embodiment of the invention, said photolabile compound generates a gas upon exposure to light at a wavelength comprised between 700 and 320 nm, preferably between 600 and 360 nm, preferably between 500 and 340 and even more preferably between 450 and 350 nm.

According to any embodiment of the invention, said photolabile compound degrades at a rate above $8.0 \times 10^{-5}$ s$^{-1}$, when exposed to UVA-light of 3.1 mW/cm$^2$ for 240 min and at a concentration of 8 mM in acetonitrile.

According to any embodiment of the invention, said photolabile compound is characterized by a calculated log P comprised between 0.5 and 6, preferably between 1.5 and 5, more preferably between 2.5 and 4.5. Said "calculated log P" is the calculated partition parameter of the photolabile compound between octanol and water and can be obtained according to the program EPI suite (4.0); EPA (US Environmental Protection Agency) and Syracuse Research Corporation (SRC), 2000.

Said photolabile compound can be included in the microcapsules in various amounts depending on its nature and the speed of release of the oil phase which is aimed. Typically, the microcapsules comprise, based on the total microcapsule weight, from about 5% to about 90% by weight, of photolabile compounds. Preferably the microcapsules comprise from about 10% to about 50% of photolabile compounds, even more preferably from 15% to about 30% of photolabile compounds.

According to any embodiment of the invention, several gas-releasing photolabile compounds can be used simultaneously as mixtures, all of which can release the same type of gas or different types of gases.

It is believed that upon exposure to light, the photolabile compound generates a gas which, in non-diffusive capsules (as defined above), causes an increase in the internal pressure leading to the release of the oil phase. The increase in internal pressure might result in an extension or breaking of the microcapsule shell or wall. The extension (swelling) of the capsule shell should make the capsule more diffusive towards the outside and thus facilitate the release of the encapsulated oil phase. Depending on the chemical structure of the capsule shell and on the speed of gas formation, the extension of the capsule shell might finally lead to a complete breaking of the capsule shell and thus allow the oil phase to leak out. All this parameter can be easily optimized by a person skilled in the art considering the thickness of the walls its chemical nature and the loading of photo-labile compound in the capsules as well as the desired speed of release.

Some photolabile compounds of formulae (i) to (iv) are commercially available, others can be prepared by generally known methods reported in the literature.

Photolabile compounds of formula (i) can be prepared by a multitude of methods, such as the oxidation of the corresponding benzylic alcohols, the coupling of aryl bromides with an acyl anion (e.g. A Takemiya and J. F. Hartwig, Journal of the American Chemical Society, 2006, vol. 128, pages 14800-14801), the condensation of benzonitriles with alkylmagnesium bromides (e.g. H. Gilman and J. Eisch, Journal of the American Chemical Society, 1957, vol. 79, pages 2150-2153) or else by a Friedel-Crafts reaction of an aryl derivative with an alkanoyl halide in the presence of a Lewis acid.

Photolabile compounds of formula (ii) wherein the two $R^4$ represent hydrogen atoms can be obtained from a methylbenzophenone as, for example, in a procedure reported by D. C. Schlegel et al. in Journal of Medicinal Chemistry, 1984, vol. 27, pages 1682-1690, those wherein the two $R^4$ taken together represent an oxygen atom bridge can, for example, be prepared from 2-iodobenzoic acid and hydroxyphenylacetic acid as described by J. C. Scaiano and co-workers in Organic Letters, 2006, vol. 8, pages 1057-1060 (and in the Supporting Information of this article).

Photolabile compounds of formula (iii) can be obtained by condensation of a chloride of formula $R^5$—X—CO—Cl with an alcohol of formula HO—$C(R^3)_2$-A, the latter of which can be obtained from the corresponding halogen derivatives Cl—$C(R^3)_2$-A or Br—$C(R^3)_2$-A or, alternatively, from the corresponding 1H-imidazole-1-carboxylate. Typical reactions of this type have been reported in the literature, e.g. by D. E. Falvey and co-workers in Tetrahedron, 1999, vol. 55, pages 12699-12710 or by P. Klán and co-workers in Photochemical and Photobiological Sciences, 2005, vol. 4, pages 43-46. If both $R^3$ are a hydrogen atom, an alcohol of formula HO—$CH_2$-A, can also be obtained from a compound of formula $H_3C$-A by preparing in a first step an aldehyde of formula OHC-A, which is then reduced to the alcohol as, for example, described in M. Petit et al., in Organic Letters, 2002, vol. 14, pages 6366-6369 (and in the Supporting Information of this article).

Photolabile compounds of formula (iv) can, for example, be prepared by reaction of a compound of formula $R^6$—$C_6H_4$—$NH_2$ with a $HN(R^7)_2$ derivative as reported by D. H. Sieh et al. in Journal of the American Chemical Society, 1980, vol. 102, pages 3883-3887 or by I. Manolov et al. in Pharmazie, 2006, vol. 61, pages 511-516.

The efficiency of generating a gas from said photolabile compound upon exposure to the light can be influenced by energy transfer via a photo-catalyst, said photo-catalyst can act via various mechanisms such as by photosensitation, photocatalysis or by photo-assisted catalysis. As defined by the International Union of Pure and Applied Chemistry (IUPAC) in Pure and Applied Chemistry, 2006, vol. 79, pages 293-465, the term "photosensitation" stands for a "photochemical or photophysical alteration occurring in one molecular entity as a result of initial absorption of radiation by another molecular entity called a "photosensitizer", "photocatalysis" means a "change in the rate of a chemical reaction or its initiation under the action of ultraviolet, visible, or infrared radiation in the presence of a substance— the photocatalyst—that adsorbs light and is involved in the chemical transformation of the reaction partners". Similarly, the term "photo-assisted catalysis" has been defined by the same source as a "catalytic reaction involving production of a catalyst by absorption of ultraviolet, visible or infrared radiation".

The component a) of the microcapsule according to the invention therefore optionally also comprises at least one photo-catalyst. The choice of a suitable photo-catalyst depends on the structure of the gas-generating photolabile compound and on the medium in which the photoreaction is supposed to take place. Said photo-catalysts are therefore of various chemical structures and are well known by a person skilled in the art; typical examples are easily found in the literature (e.g. M. Wainwright, "Photosensitizers in Biomedicine", John Wiley & Sons, Chichester, 2009, or G. K. Castello (Ed.), "Handbook of Photocatalysts: Preparation, Structure and Applications", Materials Science and Technologies Series, Nova Science Publishers, New York, 2010, or in other work of a similar nature, as well as in the abundant patent literature in the field of photosensitation or photocatalysis).

Said photo-catalyst can be included in various amounts depending on its nature and the speed of release of the oil phase which is aimed. Typically, the microcapsules comprise, based on the total microcapsule weight, from about 0.01% to about 50% by weight, of photo-catalyst. Preferably the microcapsules comprise from about 1% to about 20% of photo-catalyst.

The component b) of the microcapsules according to the invention is an interfacial shell that can be obtained by a variety of processes.

According to any embodiment of the invention, said shell is based on aminoplast, polyamide, polyester, polyurea or polyurethane resins or a mixture thereof. Said resins and shells are well known to a person skilled in the art.

According to any embodiment of the invention, such a shell is preferably obtained by a phase separation process induced by polymerization, by interfacial polymerization, by coacervation or altogether. Such processes have been described in the prior art. Such a process can, for example, be based on amino resins produced by the polycondensation of an aldehyde (e.g. formaldehyde, 2,2-dimethoxyethanal, glyoxal, glyoxylic acid or glycolaldehyde and mixtures thereof) with an amine, namely urea, benzoguanamine, glycoluril, melamine, methylol melamine, methylated methylol melamine, guanazole and the like, as well as mixtures thereof. Examples for suitable ureas are dimethylol urea, methylated dimethylol urea, urea-resorcinol, and mixtures thereof.

Some of the seminal literature related to encapsulation of perfumes by polycondensation of amino resins, namely melamine based resins, with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinency, which also address the suitable uses of such microcapsules, are represented for example by the article of H. Y. Lee et al. in Journal of Microencapsulation, 2002, vol. 19, pages 559-569, international patent publication WO 01/41915 or yet the article of S. Bone et al. in Chimia, 2011, vol. 65, pages 177-181.

The polycondensation of an aldehyde with an amine or an amino resin leads to shells or walls consisting of highly cross-linked resins known as thermoset resins (aminoplast resins). Suitable alkylolated polyamines for the microcapsules according to the invention encompass mixtures of mono- or polyalkylolated polyamines, which in turn may be partially alkylated with alcohols having from 1 to 6 methylene units, and also encompass mono- or polymethylolmelamine and/or mono- or polymethylolurea precondensates, such as those commercially available under the trademark Urac® (origin: Cytec Technology Corp.), Cymel® (origin: Cytec Technology Corp.), Urecoll® or Luracoll® (origin: BASF).

Other suitable amino resins from the mixtures of mono- or polyalkylolated polyamines can be obtained by polycondensation of an aldehyde such as 2,2-dimethoxyethanal, glyoxal, glyoxylic acid or glycolaldehyde and mixtures thereof, and an amine, as described in WO 2011/161618. Non-limiting examples of polyalkylolated polyamines from the polycondensation with 2,2-dimethoxyethanal comprise poly [N-(2,2-dimethoxy-1-hydroxy)] polyamines, mono- and di- [N-(2,2-dimethoxy)-1-hydroxy)] urea, mono-, di-, tri-, and/ or tetra-[N-(2,2-dimethoxy)-1-hydroxy)] melamine, tetra- [N-(2,2-dimethoxy)-1-hydroxy)]glycouryl or di-[N-(2,2-dimethoxy)-1-hydroxy)]benzoguanidine. Non-limiting examples of polyalkylolated polyamines from the polycondensation with glyoxal comprise poly[N-(2-hydroxyacetaldehyde)] polyamines, mono- and di-[N-(2-hydroxyacetaldehyde)] urea, mono-, di-, tri-, and/or tetra-[N-(2-hydroxyacetaldehyde)] melamine, tetra-[N-(2-hydroxyacetaldehyde)]glycouryl or di-[N-(2-hydroxyacetaldehyde)]benzoguanidine. Non-limiting examples of polyalkylolated polyamines from the polycondensation with glyoxylic acid comprise poly[N-(2-hydroxyacetic acid)] polyamines, mono- and di-[N-(2-hydroxyacetic acid)] urea, mono-, di-, tri-, and/or tetra-[N-(2-hydroxyacetic acid)] melamine, tetra-[N-(2-hydroxyacetic acid)]glycouryl or di-[N-(2-hydroxyacetic acid)]benzoguanidine. Non-limiting examples of polyalkylolated polyamines from the polycondensation with glycolaldehyde comprise poly[N-(ethane-1,2-diol)] polyamines, mono- and di-[N-(ethane-1, 2-diol)] urea, mono-, di-, tri-, and/or tetra-[N-(ethane-1,2-diol)] melamine, tetra-[N-(ethane-1,2-diol)]glycouryl or di-[N-(ethane-1,2-diol)]benzoguanidine.

According to an embodiment of the invention, core-shell microcapsules are obtained by interfacial polymerization, in which the core is encapsulated into a crosslinked polyurea or polyurethane shell or wall formed by reaction of an amino resin, a polyamine or polyol with at least one polyisocyanate.

A polyurea microcapsule shell or wall is formed when a polyamine or an amino resin is used. Particularly efficient polyamines are water soluble guanidine salts and/or guanidine and/or amino resins such as those described above. By "water soluble guanidine salt" it is meant a salt soluble in water and resulting from the reaction of guanidine with an acid. One example of such salts is guanidine carbonate.

In the case where a polyol is used as the cross-linker, a polyurethane microcapsule shell or wall is formed. As polyol, glycerol is preferred.

The use of specific proportions of polyisocyanate versus polyamine or polyol is advantageous. Therefore, preferably, for each mole of isocyanate group, 1 to 10, preferably 2 to 5 moles of amine or alcohol groups are present. Accordingly, there is added an excess of the cross-linking agent.

When a polyisocyanate compound is reacted with an amino resin, e.g. obtained by a phase separation process as described above, a polyamine or a polyol, any polyisocyanate is suitable for the reaction, but a polyisocyanate comprising at least two isocyanate groups or at least three isocyanate groups is preferred. Low volatility polyisocyanate molecules are preferred because of their low toxicity. In particular, the polyisocyanate can advantageously be selected from the group consisting of a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate are even more preferred.

For the sake of clarity, by the expression "dispersion", in the present invention, it is meant a system in which particles are dispersed in a continuous phase of a different composition, and this term specifically includes a suspension or an emulsion.

A polymeric stabilizer can be used to prevent the microcapsules from agglomerating, thus acting as a protective colloid which is added to the monomer mixture, intended to form the shell, prior to polymerization. For the sake of clarity, in the present context by the expression "stabilizer", or similar, it is understood the meaning usual in the art, i.e. a compound that is capable of, or is added to, stabilize the system, e.g. to prevent aggregation or agglomeration of the microcapsules, for example in the consumer product application or during the process for the microcapsule preparation. The use of said stabilizer is standard knowledge to the person skilled in the art.

For the purpose of the present invention, said stabilizer can be an ionic or non-ionic surfactant or a colloidal stabilizer. The exact nature of such stabilizers is well known to a person skilled in the art. As non-limiting examples one may cite the following stabilizers: non-ionic polymers such as polyvinyl alcohol (Mowiol 18-88, Origin: Fluka), cellulose derivatives such hydroxyethyl cellulose or carboxymethyl cellulose such as Ambergum™ 1221 (origin: Aqualon Hercules), polyethylene oxide, co-polymers of polyethylene oxide and polyethylene or polypropylene oxide, co-polymers of alkyl acrylates and N-vinylpyrrolidone; ionic polymers such as acrylic copolymers of acrylamide and acrylic acid such as Alcapsol® 144 (origin: Ciba), e.g. acid/acrylamide copolymers produced from a monomer mixture of acrylic acid and acrylamide wherein the acrylic acid content is in the range of from 20 to 80%, acid anionic surfactants (such as sodium dodecyl sulfate), acrylic co-polymers bearing a sulfonate group (such as sodium poly(styrene sulfonate), and co-polymers of vinyl ethers and maleic anhydride.

Optionally, the microcapsules may be coated with a cationic copolymer. The cationic polymer allows partial or complete neutralization of the negative electrical charge borne by the microcapsules, or even the conversion of the negatively-charged microcapsules into positively-charged microcapsules. To this effect, according to the invention, preferred cationic polymers comprise cationic polyacrylates and acrylamides such as Salcare® SC60 (origin: BASF), cationic cellulose derivatives, such as those available under the trademark Ucare® (origin: Amerchol), and quaternized guar gums available under the trademark Jaguar® (origin: Rhodia). Other cationic compounds that can be used include the polyquaternium compounds, all which have a plurality of quaternary ammonium groups, or polymeric species such as diallyl dimethyl ammonium chloride/acrylamide polymers such as those available under the trade name Merquat® (origin: Nalco).

According to any embodiment of the invention, if the oil phase to be encapsulated by a polymerization process is hydrophobic (e.g. with the logarithm of its octanol/water partition coefficient (log P)>1, preferably >2), it will be included in the water-immiscible phase, whereafter the two phases are mixed by high shear mixing to form an oil-in-water emulsion. In this emulsion, the polymerization will take place at the interface between the two phases. Thus, the oil droplets will be surrounded by the microcapsule shell formed by the polymerization process.

According to any embodiment of the invention, the average size of the microcapsules may range between 1 micrometer to 100 micrometers, or even more, depending on the mixing shear stress applied to the system during microcapsule formation. The selection of the most appropriate range and distribution of size depends on the application for which the microcapsules are intended, and can be controlled and adjusted by the skilled person as a function of the latter. In a general manner the average size of the microcapsules according to the invention ranges between 1 micrometer and 600 micrometers and, more preferably, comprises a range of 1 to 200 micrometers.

The phase separation process induced by polymerization and the interfacial polymerization process described above essentially convert emulsions, consisting of a dispersed oil phase, containing the photolabile compound and, optionally, the photo-catalyst to be encapsulated and a continuous water phase, into a dispersion of solid beads consisting of a core surrounded by a shell, whose permeability depends on a number of factors, including the extent of cross-linking, and/or the thickness of the shell. A person skilled in the art is able to easily find optimal factors and conditions to obtain non-diffusive capsules as required by the present invention.

According to any embodiment of the invention, the invention's microcapsules obtained either by phase separation polycondensation or by interfacial polymerization have a shell thickness varying between 10 to 1000 nm, preferably between 20 and 500 nm, even more preferably between 25 and 350 nm. As an example, the capsule's shell thickness can be determined by atomic force microscopy (AFM) or scanning electron microscopy (SEM).

According to any embodiment of the invention, the microcapsules of the present invention may be characterized by a nominal shell to core mass ratio lower than 40%, preferably lower than 20% and, most preferably, lower than 10%, the invention thus providing thin and frangible shells that allow the diffusion of the fragrance molecules resulting from the degradation of the photolabile compound.

The nominal shell to core mass ratio depends on the amount of amino resin or polyamine or polyol and/or polyisocyanate used for the preparation of the microcapsules (and thus the shell thickness of the capsule) and which has a strong influence on the performance of the delivery system. An optimum value to reach a maximum of capsule stability and the best release performance has to be reached. Specific examples according to the invention are presented further on. As an example, the nominal shell to core mass ratio can vary from 0.4 to 0.01, preferably from 0.3 to 0.02, most preferably from 0.10 to 0.03.

The microcapsules of the present invention are provided in the form of aqueous slurries, having typically 20 to 55% of solid content, where the term "solid content" is relative to the total weight of the microcapsules. Alternatively, such slurries may be spray-dried in a generally known manner to provide powder products.

The slurry may contain formulation aids, such as stabilizing and viscosity control hydrocolloids, biocides, and, as the case may be, formaldehyde scavengers.

The aqueous phase can also advantageously comprise hydrophilic inorganic particles such as silica particles or titanium oxide, in order to adjust the density of the microcapsules. By doing so, the density of the microcapsules can be brought to a value similar to that of the end product into which it is intended to incorporate them and therefore the microcapsules are maintained homogeneously suspended and dispersed in such liquid products. This is particularly advantageous in perfuming microcapsules because the specific gravity of the perfuming ingredients is usually lower than 1 g/ml.

The microcapsules according to the invention protect the oil phase against premature degradation during storage in the application formulation and increase the deposition of the oil phase on the target substrate once the latter is treated with the consumer product.

According to any embodiment of the invention, one may use the microcapsules of the present invention as a mixture with a free oil phase and/or with other microcapsules or other types of delivering technologies of the prior-art. Other microcapsules used in combination with those of the present invention can have a diffusive or non-diffusive shell.

Furthermore, the invention's microcapsules can also be advantageously used in all the fields of modern perfumery, i.e. fine or functional perfumery, to positively impart or modify the odor of a consumer product into which said invention's microcapsules are added.

Consequently, another object of the present invention is represented by a perfuming consumer product comprising:
i) as perfuming ingredient, at least one invention's microcapsule, as defined above; and
ii) as an option a perfume oil.

Such consumer product may be a solid or a liquid product. According to a particular embodiment, liquid products are preferred.

For the sake of clarity, by "consumer product" it is meant a consumer product which is typically perfumed and which is expected to deliver at least a perfuming effect, in other words it is a perfumed consumer product.

For the sake of clarity, it has to be mentioned that, by "perfuming consumer product" it is meant a consumer product which is expected to deliver at least a pleasant perfuming effect to the surface to which it is applied (e.g. skin, hair, textile, or hard surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of the microcapsules according to the present invention. It goes without saying that such a consumer product may also contain non-encapsulated perfume, i.e. perfume ingredients in free form.

The nature and type of the constituents of the consumer product do not warrant a more detailed description here, which in any case would not be exhaustive, the skilled person being able to select them on the basis of his general knowledge and according to the nature and the desired effect of said product.

Non-limiting examples of consumer products in which the microcapsules according to the invention can be used advantageously include perfumes, colognes or after-shave lotions; fabric care products, such as a liquid or solid detergents, fabric softeners or refreshers, ironing waters, tissues or other paper or cellulose based products such as nappies, and bleaches or home care products, including window and kitchen cleaners; body and hair care products (e.g. a shampoos, coloring preparations, conditioners and hair sprays), cosmetic preparations (e.g. creams, body deodorants or antiperspirants), or skin-care products (e.g. a perfumed soap, shower or bath mousse, oils or gels, or a hygiene product); an air care product, such as an air freshener or a "ready to use" powdered air freshener; or a home care product, such as a wipe, a dish detergent or hard-surface detergent.

As anticipated above, the invention's composition can be advantageously used for bringing a benefit to consumer products, such as its perfuming effect. Because some of the compounds of the oil phase described above can also have flavoring, cosmetic, skin caring, malodor counteracting, bactericide, fungicide, pharmaceutical, agrochemical, insect attractant or repellent properties, it is evident that the invention's microcapsules can also be used in formulations serving for flavoring, cosmetic, skin caring, malodor counteracting, bactericide, fungicide, pharmaceutical, agrochemical, insect attractant or repellent purposes. Indeed, said microcapsules, possess several other properties that make them particularly suitable for this purpose.

The proportions in which the microcapsules according to the invention can be incorporated into the various aforementioned consumer products vary within a wide range of values. These values are dependent on the nature of the article to be perfumed and on the desired organoleptic effect as well as the nature of the co-ingredients in a given consumer product. Typically, the consumer products comprise, based on the total consumer product weight, from about 0.01% to about 80% by weight, of microcapsules according to the present invention. Preferably the consumer products comprise from about 0.01% to about 30% of microcapsules. More preferably the consumer products comprise from about 0.1% to about 15% of microcapsules.

Formulations of consumer product in which the microcapsules of the invention can be incorporated can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

Another object of the present invention is a method for intensifying or prolonging the effect of the characteristic fragrance of a perfume ingredient on a surface, characterized in that said surface is, preferentially in the presence of light, treated with a) a microcapsule of the invention, as defined above, containing an oil phase comprising at least one photolabile compound generating, upon exposure to the light, a gas selected among the group consisting of CO, $CO_2$, $N_2$ and $C_2$-$C_4$ alkenes and, optionally, comprising at least one photo-catalyst; and
b) a perfuming composition of the invention, as defined above, comprising the microcapsule of a); or
c) a perfumed consumer product, as defined above, comprising the microcapsule of a); under conditions which are susceptible of allowing the release of the oil phase.

Suitable surfaces for such treatment are in particular textiles, hard surfaces, hair and skin.

BRIEF DESCRIPTION OF THE DRAWINGS

FIG. 1: Comparison of the amount of Romascone® released from microcapsules containing 1-phenylbutan-1-one (butyrophenone; origin: Aldrich) capable of generating a gas according to the invention prepared in Example 3 (———) and from equivalent prior-art microcapsules without butyrophenone prepared in Comparative Example 3 (• • • • • •) as determined by dynamic headspace analysis after exposure of the microcapsules to light. The position of the arrow indicates the beginning of UV light irradiation.

EXAMPLES

The invention is hereafter described in more detailed manner by way of the following examples, wherein the abbreviations have the usual meaning in the art, temperatures are indicated in degrees centigrade (° C.). NMR spectral data were recorded in $CDCl_3$ (if not stated otherwise) on a Bruker AMX 400 or 500 spectrometer at 400 or 500 MHz for $^1H$ and at 100.6 or 125.8 MHz for $^{13}C$, the chemical displacements δ are indicated in ppm with respect to $Si(CH_3)_4$ as the standard, the coupling constants J are expressed in Hz (br.=broad peak). Commercially available reagents and solvents were used without further purification if not stated otherwise. Reactions were carried out in standard glassware under $N_2$.

Although specific conformations or configurations are indicated for some of the compounds, this is not meant to limit the use of these compounds to the isomers described. According to the invention, all possible conformation or configuration isomers are expected to have a similar effect.

Example 1

Preparation of Photolabile Compounds Capable of Generating a Gas Upon Exposure to Light Preparation of 2-(9-oxo-9H-xanthen-2-yl)acetic acid A mixture of 2-iodobenzoic acid (5.00 g, 20.16 mmol, origin: Aldrich), 2-(4-hydroxyphenyl)acetic acid (4.30 g, 28.2 mmol, origin: Acros), $Cs_2CO_3$ (25 g, 77.0 mmol) in dioxane (100 mL) was stirred at room temperature. After 10 min, tris(2-(2-methoxyethoxy)ethyl)amine (0.78 g, 2.42 mmol) and CuCl (0.24 g, 2.41 mmol) were added. The mixture was heated under reflux (100° C.) for 20 h. After cooling to room temperature, the solvent was removed under reduced pressure and the remaining solid dissolved in aqueous NaOH (0.1 M, 100 mL) and filtered. The green filtrate was transferred to a separatory funnel, acidified with aqueous HCl (1 M, 33 mL) and extracted with ethyl acetate (3×30 mL). The combined organic layers were dried (Na$_2$SO$_4$) and concentrated under reduced pressure to give 7.86 g of a brown solid. Concentrated sulfuric acid (12 mL) was carefully added and the mixture heated at 85° C. for 1 h. After cooling to room temperature, the mixture was poured onto ice (70 g). The aqueous solution was transferred to a separatory funnel with water and extracted with ethyl acetate (3×30 mL). The combined organic phases were dried (Na$_2$SO$_4$) and the solvent removed under reduced pressure. The residue was dissolved in a mixture of toluene (15 mL) and methanol (3 mL) and heated at reflux (ca. 70° C.). After cooling to room temperature, the product crystallized. The product was taken up in toluene (15 mL), re-heated to reflux to dissolve and left re-crystallizing overnight to give 0.20 g (4%) of fine white crystals.

$^1$H-NMR (500 MHz, DMSO-D$_6$): δ 12.56 (br. s, 1H), 8.20 (dd, J=8.0, 1.6, 1H), 8.09 (d, J=2.3, 1H), 7.90-7.84 (m, 1H), 7.78 (dd, J=8.7, 2.3, 1H), 7.68-7.63 (m, 1H), 7.62 (d, J=8.7, 1H), 7.51-7.45 (m, 1H), 3.79 (s, 2H).

$^{13}$C-NMR (125.8 MHz, DMSO-D$_6$): δ 175.83 (s), 172.43 (s), 155.49 (s), 154.40 (s), 136.89 (d), 135.39 (d), 131.33 (s), 126.24 (d), 125.91 (d), 124.22 (d), 120.98 (s), 120.68 (s), 118.09 (d), 117.97 (d), 39.56 (t).

Preparation of ethyl(2-oxo-2-(pyren-1-yl)ethyl)carbonate

Cesium formate (8.26 g, 46.4 mmol) was dissolved in pure methanol (50 mL) at 45° C. After cooling to room temperature, 2-bromo-1-(pyren-1-yl)ethanone (5.00 g, 15.5 mmol, origin: Aldrich) was added and the mixture was heated under reflux for 4 h. The solvent was removed under reduced pressure, the residue taken up in ethyl acetate (50 mL) at 45° C. and filtered through a sintered glass frit. The filtrate was concentrated and dried under high vacuum at room temperature for 2 h to give 2.24 g of 2-hydroxy-1-(pyren-1-yl)ethanone as an orange solid.

$^1$H-NMR (500 MHz): δ 9.14 (d, J=9.3, 1H), 8.17 (d, J=7.7, 1H), 8.16 (d, J=7.7, 1H), 8.13 (d, J=9.3, 1H), 8.10 (d, J=8.0, 1H), 8.06 (d, J=9.0, 1H), 7.99 (t, J=7.7, 1 H), 7.95 (d, J=8.0, 1H), 7.90 (d, J=9.0, 1H), 5.00 (s, 2H), 3.70 (br. s, 1H).

$^{13}$C-NMR (125.8 MHz): δ 200.95 (s), 134.82 (s), 130.80 (s), 130.46 (d), 130.22 (d, 2s), 126.84 (d), 126.76 (d), 126.49 (d), 126.47 (d), 126.21 (s), 125.99 (d), 124.74 (s), 124.41 (d), 123.93 (d), 123.81 (s), 66.88 (t).

Ethyl chloroformate (0.83 g, 7.68 mmol) was added during 15 min to a mixture of 2-hydroxy-1-(pyren-1-yl)ethanone (2.0 g, 7.68 mmol), N,N-dimethylpyridin-4-amine (DMAP) (1.13 g, 9.22 mmol) in dichloromethane (20 mL). After stirring overnight at room temperature, the solvent was evaporated. Column chromatography (SiO$_2$, ethyl acetate/n-heptane 1:1) afforded 2.12 g (83%) of a yellow solid.

$^1$H-NMR (500 MHz): δ 8.96 (d, J=9.3, 1H), 8.20-8.15 (m, 3H), 8.14 (d, J=8.0, 1H), 8.07 (d, J=9.0, 1H), 8.02 (d, J=8.0, 1H), 7.99 (t, J=7.5, 1H), 7.93 (d, J=9.0, 1 H), 5.46 (s, 2H), 4.31 (q, J=7.2, 2 H), 1.37 (t, J=7.1, 3 H).

$^{13}$C-NMR (125.8 MHz): δ 195.55 (s), 155.06 (s), 134.38 (s), 130.85 (s), 130.37 (s), 130.15 (d), 130.00 (s), 129.98 (d), 127.80 (s), 126.87 (d), 126.55 (d), 126.48 (d), 126.34 (d), 125.62 (s), 124.82 (s), 124.42 (s), 123.90 (s), 123.83 (d), 70.03 (t), 64.75 (t), 14.24 (q).

Preparation of (1R,2S,5R)-2-isopropyl-5-methylcyclohexyl (2-oxo-2-(pyren-1-yl)ethyl)carbonate (−)-Menthyl chloroformate (0.84 g, 3.84 mmol, origin: Aldrich) was added during 15 min to a mixture of 2-hydroxy-1-(pyren-1-yl)ethanone (1.0 g, 3.84 mmol), DMAP (0.56 g, 4.61 mmol) in dichloromethane (20 mL). After stirring overnight at room temperature, the solvent was evaporated and the residue taken up with ethyl acetate (50 mL), washed with demineralized tap water (3×30 mL), dried (Na$_2$SO$_4$), concentrated and dried under high vacuum during 2 h to give 1.59 g of a brownish red solid. The compound still contained impurities and was thus re-dissolved in ethyl acetate (50 mL) at 40° C., washed with aqueous HCl (10%, 3×30 mL), water (30 mL) and a saturated aqueous solution of NaHCO$_3$ (30 mL). The organic phase was dried (Na$_2$SO$_4$), concentrated and dried under high vacuum during 2 h to give 1.11 g (65%) of a brownish yellow solid, still containing some impurities.

$^1$H-NMR (500 MHz): δ 8.92 (d, J=9.3, 1H), 8.25-8.19 (m, 3H), 8.19 (d, J=9.6, 1H), 8.13 (d, J=9.0. 1H), 8.11 (d, J=8.0, 1H), 8.03 (t, J=7.5, 1H), 8.01 (d, J=9.0, 1 H), 5.42 (d, J=3.2, 2 H), 4.57-4.49 (m, 1H), 2.07-2.00 (m, 1H), 1.93-1.84 (m, 1H), 1.70-1.57 (m, 2H), 1.50-1.35 (m, 2H), 1.10-0.78 (m, 3H), 0.85 (d, J=6.7, 3 H), 0.81 (d, J=6.7, 3 H), 0.66 (d, J=7.0, 3 H).

$^{13}$C-NMR (125.8 MHz): δ 196.50 (s), 154.78 (s), 134.28 (s), 130.93 (s), 130.48 (s), 130.06 (d), 129.95 (s), 129.93 (d), 128.36 (s), 126.96 (d), 126.50 (2d), 126.33 (d), 125.66 (d), 124.93 (s), 124.46 (d), 124.05 (s), 123.82 (d), 79.25 (d), 70.15 (t), 46.95 (d), 40.52 (t), 34.03 (t), 31.36 (d), 26.02 (d), 23.29 (t), 21.88 (q), 20.59 (q), 16.11 (q).

Preparation of (6-(dimethylamino)quinolin-2-yl)methyl ethyl carbonate

4-N,N-Dimethylaminoaniline (10.00 g, 73.4 mmol, origin: Alfa Aesar) was dissolved in 6 M aqueous HCl (132 mL). (E)-2-Butenal (10.30 g, 147 mmol, origin: Acros) was added and the mixture stirred at room temperature for 1 h. Then toluene (70 mL) was added and the reaction heated at reflux overnight. After cooling to room temperature, the organic layer was removed. The aqueous layer was treated with NaOH (10%, 350 mL) and extracted with dichloromethane (2×100 mL). The organic phase was washed with water (2×100 mL) and with a saturated aqueous solution of NaCl (2×), dried (Na$_2$SO$_4$), and concentrated under reduced pressure. Column chromatography (SiO$_2$, ethyl acetate) gave 8.44 g (62%) of N,N,2-trimethylquinolin-6-amine as a brown solid.

$^1$H-NMR (500 MHz): δ 7.87 (d, J=9.3, 1H), 7.83 (d, J=8.3, 1H), 7.31 (dd, J=9.3, 2.9, 1H), 7.13 (d, J=8.3, 1H), 6.76 (d, J=2.9, 1H), 3.01 (s, 6H), 2.66 (s, 3H).

$^{13}$C-NMR (125.8 MHz): δ 154.54 (s), 148.12 (s), 141.89 (s), 134.43 (d), 129.10 (d), 127.77 (s), 122.11 (d), 119.30 (d), 105.41 (d), 40.78 (q), 24.92 (q).

A solution of N,N,2-trimethylquinolin-6-amine (2.00 g, 10.7 mmol) in dioxane (15 mL) was added to a suspension of selenium dioxide (1.55 g, 14.0 mmol) in dioxane (60 mL) and water (3.4 mL) at 80° C. The mixture was left stirring at 80° C. for 3 h. After cooling to room temperature, the product was filtered on celite, washed with dichloromethane and the filtrate concentrated under reduced pressure. Column chromatography (SiO$_2$, ethyl acetate/n-heptane 1:3) gave 0.80 g (37%) of 6-(dimethylamino)quinoline-2-carbaldehyde as a brownish-yellow solid.

¹H-NMR (500 MHz): δ 10.12 (d, J=1.0, 1H), 8.03 (d, J=9.6, 1H), 7.97 (d, J=8.3, 1 H), 7.88 (d, J=8.3, 1H), 7.39 (dd, J=9.3, 2.9, 1H), 6.76 (d, J=2.9, 1H), 3.13 (s, 6H).

¹³C-NMR (125.8 MHz): δ 193.47 (d), 150.17 (s), 148.85 (s), 141.69 (s), 134.21 (d), 132.22 (s), 131.28 (d), 119.70 (d), 118.09 (d), 103.83 (d), 40.37 (q).

6-(Dimethylamino)quinoline-2-carbaldehyde (0.70 g, 3.5 mmol) was dissolved in ethanol (35 mL) and cooled to 0° C. before sodium borohydride (0.15 g, 3.85 mmol) was added. The solution was stirred for 1 h at room temperature and the reaction followed by TLC. Aqueous HCl (10%, ca. 50 drops) was added dropwise until the solution turned orange.

The solvent was removed under reduced pressure and the residue taken up in dichloromethane (40 mL). The mixture was washed water (2×30 mL), a saturated aqueous solution of NaCl (2×) and dried (Na₂SO₄). The solvent was removed under reduced pressure and the product dried under high vacuum (2 h) to give 0.69 g (98%) of (6-(dimethylamino)quinolin-2-yl)methanol as an orange solid.

¹H-NMR (500 MHz): δ 7.91 (d, J=8.4, 1H), 7.90 (d, J=9.3, 1H), 7.33 (dd, J=9.3, 2.9, 1H), 7.15 (d, J=8.7, 1H), 6.80 (d, J=2.9, 1H), 4.84 (s, 2H), 4.48 (br. s, 1H), 3.05 (s, 6H).

¹³C-NMR (125.8 MHz): δ 154.74 (s), 148.54 (s), 140.70 (s), 135.01 (d), 129.10 (d), 128.99 (s), 119.40 (d), 118.63 (d), 105.33 (d), 64.15 (t), 40.73 (q).

Ethyl chloroformate (0.27 g, 2.52 mmol) was added during 15 min to a solution of (6-(dimethylamino)quinolin-2-yl)methanol (0.51 g, 2.52 mmol) and DMAP (0.37 g, 3.03 mmol) in dichloromethane (20 mL). The mixture was stirred at room temperature for 4 h, before more ethyl chloroformate (0.2 mL) was added. The mixture turned dark and the reaction was stirred at room temperature for 1 h. The solvent was removed under reduced pressure to give a brownish-orange solid, which was taken up in ethyl acetate (12 mL) and water (2 mL). The mixture was stirred for 30 min, before Na₂SO₄ was added. After filtration, the mixture was concentrated under reduced pressure to ca. 4 mL and n-heptane (1 mL) was added. Column chromatography of the solution (SiO₂, n-heptane/ethyl acetate 1:1) gave 0.28 g (40%) of a brownish-yellow oil.

¹H-NMR (600 MHz): δ 7.96 (d, J=8.5, 1H), 7.92 (d, J=9.2, 1H), 7.38 (d, J=8.5, 1H), 7.36 (dd, J=9.2, 3.1, 1H), 6.78 (d, J=3.1, 1H), 5.38 (s, 2H), 4.25 (q, J=7.2, 2 H), 3.07 (s, 6H), 1.33 (t, J=7.1, 3 H).

¹³C-NMR (151.0 MHz): δ 155.12 (s), 150.99 (s), 148.72 (s), 141.63 (s), 134.93 (d), 129.75 (d), 129.19 (s), 119.79 (d), 119.64 (d), 104.79 (d), 70.68 (t), 64.27 (t), 40.66 (q), 14.29 (q).

Preparation of ethyl(2-oxo-2-phenylethyl)carbonate

Ethyl chloroformate (8.0 g, 73.6 mmol) was added dropwise to a vigorously stirred solution of 2-hydroxy-1-phenylethanone (5.0 g, 36.8 mmol, origin: Acros) in pyridine (50 g). The reaction was heated at 80° C. for 1 h and left cooling to room temperature for 1 h.

The mixture was poured onto ice and aqueous H₂SO₄ (25%, 200 mL), extracted with diethylether (150 mL), washed with aqueous H₂SO₄ (10%, 100 mL), a saturated aqueous solution of NaHCO₃ (2×100 mL) and water (2×100 mL). The organic phase was dried (Na₂SO₄) and concentrated under reduced pressure (45° C.) to give 7.1 g of an orange-yellow oil as the crude product. Column chromatography (SiO₂, ethyl acetate/n-heptane 1:3) gave 6.82 g (89%) of an orange-yellow oil.

¹H-NMR (600 MHz): δ 7.94-7.89 (m, 2H), 7.64-7.59 (m, 1H), 7.52-7.47 (m, 2H), 5.35 (s, 2H), 4.27 (q, J=7.2, 2 H), 1.35 (t, J=7.1, 3 H).

¹³C-NMR (151.0 MHz): δ 191.88 (s), 154.87 (s), 134.02 (d), 128.92 (d), 127.75 (d), 68.51 (t), 64.73 (t), 14.21 (q).

Preparation of
(9,10-dioxo-9,10-dihydroanthracen-2-yl)methyl ethyl carbonate

Ethyl chloroformate (0.91 g, 8.39 mmol) was added during 15 min to a mixture of 2-hydroxymethylanthraquinone (2.00 g, 8.39 mmol, origin: Sigma) and DMAP (1.23 g, 10.1 mmol) in dichloromethane (20 mL). After stirring overnight at room temperature, the solvent was evaporated to give a brown paste. Column chromatography (SiO₂, ethyl acetate/n-heptane 3:7) afforded 1.15 g (44%) of a yellow solid.

¹H-NMR (500 MHz): δ 8.32-8.27 (m, 4H), 7.83-7.77 (m, 3H), 5.31 (s, 2H), 4.26 (q, J=7.2, 2 H), 1.34 (t, J=7.2, 3 H).

¹³C-NMR (125.8 MHz): δ 182.75 (s), 182.67 (s), 154.90 (s), 142.06 (s), 134.22 (d), 134.18 (d), 133.68 (s), 133.45 (s), 133.43 (s), 133.22 (s), 132.91 (d), 127.77 (d), 127.29 (d), 127.25 (d), 126.15 (d), 68.09 (t), 64.56 (t), 14.25 (q).

Example 2

Degradation of Photolabile Compounds Capable of Generating a Gas Upon Exposure to Light The photolabile compounds capable of generating a gas upon exposure to light according to the invention (0.08 mmol) were each dissolved in acetonitrile (10 mL). An aliquot of this solution (5 mL) was placed inside a Pyrex test tube (14 mL total volume) and closed with a grinded stopper. The solution was then irradiated with a xenon lamp (Heraeus Suntest CPS at about 45000 lux, corresponding to 3.1 mW/cm² of UVA-light) for 30 min. High performance liquid chromatography (HPLC) was used to quantify the degradation of the product before and after irradiation. The measurements were carried out on a Thermo Separation Products instrument composed of a SpectraSystem SCM1000 online vacuum degasser, a SpectraSystem P4000 quaternary pump, a SpectraSystem AS3000 autosampler and a SpectraSystem UV6000LP diode array detector. For the analysis, the solution (50 μL) was diluted with acetonitrile (950 μL) and injected (10 μL) onto a Macherey-Nagel Nucleosil 120-5 C4 (250×4 mm) column and eluted at 1 mL/min with a gradient of water/acetonitrile (containing 0.1% of trifluoroacetic acid) moving from 50:50 to 20:80 (during 5 min) with UV detection at 254 nm. The results of the measurements are summarized in Table 1; the reported percentages correspond to the relative HPLC peak areas before and after exposure to light for 30 min.

TABLE 1

Degradation of photolabile compounds in solution upon exposure to light

| Photolabile compound irradiated | Amount of remaining photolabile compound after exposure to light for 30 min |
|---|---|
| Butyrophenone | 76% |
| 2-(9-Oxo-9H-xanthen-2-yl)acetic acid | 62% |
| ethyl (2-oxo-2-(pyren-1-yl)ethyl) carbonate | 85% |
| (6-(Dimethylamino)quinolin-2-yl)methyl ethyl carbonate | 81% |

TABLE 1-continued

Degradation of photolabile compounds in solution upon exposure to light

| Photolabile compound irradiated | Amount of remaining photolabile compound after exposure to light for 30 min |
|---|---|
| Ethyl (2-oxo-2-phenylethyl) carbonate together with 9,10-dimethylanthracene (1.2 eq.) as photosensitizer | 53% |
| (9,10-Dioxo-9,10-dihydroanthracen-2-yl)methyl ethyl carbonate | 55% |

The rate of degradation of butyrophenone was measured by HPLC using the conditions described above. Before irradiation ($t_0$) a first aliquot of the solution (50 μL) was pipetted off, diluted with acetonitrile (950 μL) and analyzed. Then the lamp was switched on, and further aliquots of the solutions were pipetted off (every 10 min during 1 h, then every 20 min during another 3 h), diluted and analyzed as described above.

Observed first-order rate constants ($k_{obs}$) were obtained according to Equation 1 by plotting the negative natural logarithm of the (decreasing) peak areas measured at time t ($A_t$) over the one measured at time $t_0$ ($A_0$) against time.

$$A_t = A_0 e^{(-k_{obs} t)} \quad \text{(Eq. 1)}$$

Linear regression gave a straight line with a correlation coefficient ($r^2$) of 0.985 and an observed first-order rate constant ($k_{obs}$) of $8.81 \times 10^{-5}$ s$^{-1}$.

The data show that the photolabile compounds rapidly degrade after exposure to light.

Example 3

Preparation of Microcapsules a According to the Present Invention Containing a Photolabile Compound Capable of Generating a Gas Upon Exposure to Light and a Fragrance Molecule as the Oil Phase In a beaker, a polyisocyanate (Takenate® D-110N, Trimethylol propane-adduct of xylylene diisocyanate, origin Mitsui Chemicals, 2.35 g) and photolabile 1-phenylbutan-1-one (butyrophenone, origin: Aldrich, 8.76 g) were dissolved in Romascone® (methyl 2,2-dimethyl-6-methylene-1-cyclohexanecarboxylate, origin: Firmenich SA, 4.38 g) and Hedione® HC (methyl 2-((1S,2R)-3-oxo-2-pentylcyclopentyl)acetate, origin: Firmenich SA, 4.39 g). The oil phase was added to a solution of poly(vinyl alcohol) (circa 0.43 g, PVOH 18-88, origin: Aldrich) at 1 wt % in water (circa 42 mL). An emulsion was prepared by Ultra-Turrax stirring (model S25N 10G) between 15'000 and 24'000 rpm for 2 min. The droplet size was controlled by light microscopy. The emulsion was then introduced at room temperature into a 250 mL reactor and stirred with an anchor at 350 rpm. A solution of guanazole (1H-1,2,4-Triazole-3,5-diamine, origin: Alfa Aesar, 0.43 g) in water (circa 5 mL) was added dropwise onto the emulsion for 1 h. The reaction mixture was heated from room temperature to 70° C. during 1 h at pH 5, and then kept at 70° C. for 2 h, and finally cooled to room temperature to afford a white dispersion.

Comparative Example 3

Preparation of Comparative Microcapsules a without an Invention's Photolabile Compound (Microcapsules According to the Prior Art)

In a beaker, a polyisocyanate (Takenate® D-110N, origin Mitsui Chemicals, 3.52 g) and Romascone® (8.77 g) were dissolved in Hedione® HC (8.75 g). The oil phase was added to a solution of PVOH 18-88 (circa 0.44 g) at 1 wt % in water (circa 42 mL). An emulsion was prepared by Ultra-Turrax stirring (model S25N 10G) between 15'000 and 24'000 rpm for 2 min. The droplet size was controlled by light microscopy. The emulsion was then introduced at room temperature into a 250 mL reactor and stirred with an anchor at 350 rpm. A solution of guanazole (0.65 g) in water (circa 5 mL) was added dropwise onto the emulsion for 1 h. The reaction mixture was heated from room temperature to 70° C. during 1 h at pH 5, and then kept at 70° C. for 2 h, and finally cooled to room temperature to afford a white dispersion.

Example 4

Release of the Oil Phase from the Microcapsules after Exposure to Light
General Protocol Dispersions of Microcapsules A and Comparative Microcapsules A, obtained as described in Example 3 and Comparative Example 3, were diluted in water to have the same concentration of fragrance in the oil phase. An aliquot of these dispersions was put onto a glass slide (Table 2) and kept at room temperature in the dark for 96 h. The glass slide was then placed inside a headspace sampling cell (ca. 500 mL of inner volume), and exposed to a constant air flow of ca. 200 mL/min. The air was filtered through activated charcoal and aspirated through a saturated solution of NaCl to give a constant humidity of ca. 75%. Glass slides were irradiated with xenon light (Heraeus Suntest CPS at about 45000 lux), respectively. The evaporated volatiles were adsorbed for 10 min on a clean Tenax® cartridge (0.10 g) every 15 min. The cartridges were thermally desorbed on a Perkin Elmer TurboMatrix ATD thermodesorber, injected onto a Agilent Technologies 7890A System gas chromatograph equipped with a HP-1 capillary column and eluted using a temperature gradient starting at 60° C., then heating to 200° C. at 15° C./min. The amount of fragrances released was quantified by external standard calibration. The results obtained for the irradiation of the different samples are summarized in FIG. 1.

TABLE 2

Composition of dispersion put on glass slide for headspace analysis

| Dispersion | Mass of dispersion [g] | Mass of water [g] | Concentration of volatile (wt %) |
|---|---|---|---|
| Comparative Example 3 (Prior art) | 0.100 | 5.000 | 0.513 |
| Example 3) | 0.101 | 5.310 | 0.504 |

The data in FIG. 1 demonstrate that considerably higher headspace concentrations of perfume oil were measured in the headspace above Microcapsules A containing photolabile butyrophenone according to the invention as compared to an equivalent prior art microcapsule. In addition, before exposure to light the headspace concentration of perfume oil released from Microcapsule A of the present invention was as low as the headspace concentration of perfume oil released from microcapsules of the prior art. The exposure to light initiated the degradation of the butyrophenone by forming a gas and, as a consequence, triggered the release of the perfume oil (concentrations before and after the arrow in FIG. 1). The presence of a gas-generating photolabile compound according to the invention is thus suitable to efficiently trigger the release of an encapsulated oil phase without requiring scratching or rubbing the microcapsules to mechanically break their shell.

The invention claimed is:

1. A non-diffusive core-shell microcapsule comprising:
   a) a core comprising:
      an oil phase;
      at least one photolabile compound capable of generating, upon exposure to light at a wavelength comprised between 900 and 300 nm, a gas selected among the group consisting of $C_2$-$C_4$ alkenes;
   wherein the at least one photolabile compound comprises an alkyl aromatic ketone of formula:

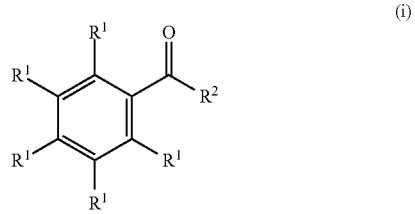

wherein each $R^1$ represents, independently of each other, a hydrogen atom, a fluorine or chlorine atom, a hydroxyl or amino group or a $C_{1-2}$ alkyl, $C_{1-2}$ alkoxy, $C_{1-2}$ dialkylamino or $COR^{2'}$ group wherein $R^{2'}$ represents a hydrogen atom or a $C_{1-4}$ alkyl group, provided that at least two $R^1$ represent a hydrogen atom; or two adjacent $R^1$, when taken together, represent a $OCH_2O$ group, a $OCH_2CH_2O$ group or a $C_{3-4}$ alkanediyl group, optionally substituted with one to four methyl groups; and wherein $R^2$ represents a propyl, n-butyl, or sec-butyl group; and
   optionally comprising at least one photo-catalyst; and
   b) a shell surrounding said core having a wall thickness of between 10 and 350 nm and being formed by interfacial polymerization or by a phase separation process induced by polymerization or by coacervation,
   wherein exposure of the microcapsule to light having a wavelength of between 900 and 300 nm generates a gas in the core that causes breakage of the shell to allow a greater release of the oil phase than microcapsules that do not contain the at least one photolabile compound.

2. The microcapsule according to claim 1, which comprises, based on the total microcapsule weight, from about 10% to about 50% of photolabile compounds.

3. The microcapsule according to claim 1, which comprises, based on the total microcapsule weight, from about 20% to about 96% of oil phase.

4. The microcapsule according to claim 1, wherein the photo-catalyst is present and comprises from 1% to 20% based on the total microcapsule weight.

5. The microcapsule according to claim 1, wherein the shell surrounding the core is an aminoplast, polyamide, polyester, polyuria or polyurethane resins or a mixture thereof.

6. The microcapsule according to claim 1, wherein the shell has a thickness varying between 25 and 350 nm.

7. The microcapsule according to claim 1, wherein the oil phase comprises a perfuming oil.

8. The microcapsule according to claim 1, wherein the photolabile compound is butyrophenone, 4-methoxybutyrophenone, 4-hydroxybutyrophenone, 3,4-(methylenedioxy) butyrophenone, valerophenone, 2-hydroxyvalerophenone, 4-hydroxyvalerophenone or isovalerophenone.

9. The microcapsule according to claim 1, wherein the photolabile compound is butyrophenone.

10. A consumer product comprising:
    i) as a perfuming ingredient, at least one microcapsule as defined in claim 7; and
    ii) optionally, a free perfume oil.

11. The consumer product according to claim 10, in the form of a perfume, a fabric care product, a body-care product, an air care product or a home care product.

12. The consumer product according to claim 10, in the form of a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

13. A consumer product comprising:
    i) as a perfuming ingredient, at least one microcapsule as defined in claim 9; and
    ii) optionally, a free perfume oil.

14. The consumer product according to claim 13, in the form of a perfume, a fabric care product, a body-care product, an air care product or a home care product.

15. The consumer product according to claim 13, in the form of a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

16. The non-diffusive core-shell microcapsule according to claim 1, wherein:
    the core consists of a perfuming oil, the at least one photolabile compound and, optionally, the photocatalyst.

17. The microcapsule according to claim 7, wherein the photolabile compound is butyrophenone.

18. The microcapsule according to claim 17, wherein the oil phase comprises a perfuming oil.

19. The microcapsule according to claim 18, wherein the photolabile compound is butyrophenone.

20. A method of releasing a perfuming oil from a non-diffusive core-shell microcapsule, which comprises:
    providing the perfume oil in a microcapsule that has a core and shell surrounding the core, wherein the core comprises:
    at least one photolabile compound capable of generating, upon exposure to light at a wavelength comprised between 900 and 300 nm, a gas selected among the group consisting of $C_2$-$C_4$ alkenes, wherein the at least one photolabile compound comprises an alkyl aromatic ketone of formula:

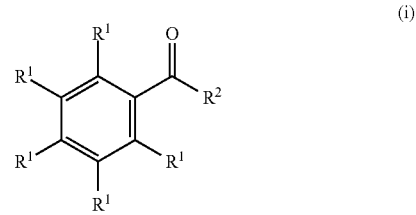

wherein each $R^1$ represents, independently of each other, a hydrogen atom, a fluorine or chlorine atom, a hydroxyl or amino group or a $C_{1-2}$ alkyl, $C_{1-2}$ alkoxy, $C_{1-2}$ dialkylamino or $COR^{2'}$ group wherein $R^2$ represents a hydrogen atom or a $C_{1-4}$ alkyl group, provided that at least two $R^1$ represent a hydrogen atom; or two adjacent R', when taken together, represent a $OCH_2O$ group, a $OCH_2CH_2O$ group or a $C_{3-4}$ alkanediyl group, optionally substituted with one to four methyl groups; and wherein $R^2$ represents a propyl, n-butyl, or sec-butyl group; and optionally, at least one photo-catalyst;

forming the shell about the core with a wall thickness of between 10 and 350 nm by interfacial polymerization or by a phase separation process induced by polymerization or by coacervation, and exposing the microcapsule to light having a wavelength of between 900 and 300 nm to generate a gas in the core in an amount sufficient to cause breakage of the shell to allow a greater release of the perfume oil than microcapsules that do not contain the at least one photolabile compound.

21. The method of claim 20 wherein the photolabile compound is butyrophenone.

* * * * *

UNITED STATES PATENT AND TRADEMARK OFFICE
CERTIFICATE OF CORRECTION

| | |
|---|---|
| PATENT NO. | : 10,646,416 B2 |
| APPLICATION NO. | : 14/893526 |
| DATED | : May 12, 2020 |
| INVENTOR(S) | : Herrmann et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 333 days.

Signed and Sealed this
Thirteenth Day of December, 2022

Katherine Kelly Vidal
*Director of the United States Patent and Trademark Office*